(12) United States Patent
Patricelli et al.

(10) Patent No.: US 7,680,679 B1
(45) Date of Patent: *Mar. 16, 2010

(54) METHOD AND SYSTEM FOR PROCESSING TRANSACTIONS INVOLVING ACCOUNTS FOR REIMBURSING MEDICAL EXPENSES OR PATIENT RESPONSIBLE BALANCES WITH MULTIPLE TRANSACTION SUBSTANTIATION MODES

(75) Inventors: Robert E. Patricelli, Simsbury, CT (US); Matthew J. Dallahan, Vernon, CT (US); Kent F. Rausch, LaGrange, KY (US)

(73) Assignee: Evolution Benefits, Inc., Avon, CT (US)

( * ) Notice: Subject to any disclaimer, the term of this patent is extended or adjusted under 35 U.S.C. 154(b) by 456 days.

This patent is subject to a terminal disclaimer.

(21) Appl. No.: 11/698,026

(22) Filed: Jan. 26, 2007

Related U.S. Application Data

(63) Continuation of application No. 10/739,218, filed on Dec. 19, 2003, now Pat. No. 7,197,468, which is a continuation-in-part of application No. 09/878,891, filed on Jun. 11, 2001, now Pat. No. 7,174,302.

(51) Int. Cl.
*G06Q 50/00* (2006.01)
(52) U.S. Cl. ................... 705/2; 705/4; 705/39
(58) Field of Classification Search .............. 705/2, 705/4, 39
See application file for complete search history.

(56) References Cited

U.S. PATENT DOCUMENTS

| | | | |
|---|---|---|---|
| 5,253,164 A | 10/1993 | Holloway et al. | 705/2 |
| 5,384,449 A | 1/1995 | Peirce | 235/380 |
| 5,550,734 A | 8/1996 | Tarter et al. | 364/401 |
| 5,644,778 A | 7/1997 | Burks et al. | 705/2 |
| 5,689,100 A | 11/1997 | Carrithers et al. | 235/380 |
| 5,704,044 A | 12/1997 | Tarter et al. | 705/4 |
| 5,903,881 A | 5/1999 | Schrader et al. | 705/42 |
| 5,914,472 A | 6/1999 | Foladare et al. | 235/380 |
| 5,930,759 A | 7/1999 | Moore et al. | 705/2 |
| 5,991,750 A | 11/1999 | Watson | 705/44 |
| 6,012,035 A | 1/2000 | Freeman, Jr. et al. | 705/2 |

(Continued)

OTHER PUBLICATIONS

"Evolution Benefits Announces 2004 Technology Plans, Building on Industry Leading Capabilities, Announcement Also Corrects the Record on Substantiation Claims of Other Debit Card Companies," *Internet Wire*, Mar. 24, 2004.

(Continued)

*Primary Examiner*—Gerald J. O'Connor
*Assistant Examiner*—Lena Najarian
(74) *Attorney, Agent, or Firm*—Kilpatrick Stockton LLP

(57) ABSTRACT

The present invention relates to a method and system for processing transactions involving accounts for reimbursing medical expenses or patient responsible balances, wherein the accounts may be handled by multiple payors having multiple transaction substantiation requirements. Examples of such accounts include flexible spending accounts, health reimbursement arrangement accounts, medical savings account, health savings account and the like. The system and method of the present invention allow an employer that uses multiple payors for administering the aforementioned accounts to distinguish its employees based on their associated payors in order to determine the proper transaction substantiation requirement per each employee and associated payor without having required to collect payor data at the employee level.

20 Claims, 6 Drawing Sheets

U.S. PATENT DOCUMENTS

| | | | | |
|---|---|---|---|---|
| 6,029,144 | A | 2/2000 | Barrett et al. | 705/30 |
| 6,044,352 | A | 3/2000 | Deavers | 705/4 |
| 6,044,360 | A | 3/2000 | Picciallo | 705/21 |
| 6,067,522 | A | 5/2000 | Warady et al. | 705/2 |
| 6,108,641 | A | 8/2000 | Kenna et al. | 705/35 |
| 6,208,973 | B1 | 3/2001 | Boyer et al. | 705/2 |
| 6,226,624 | B1 | 5/2001 | Watson et al. | 705/44 |
| 6,253,998 | B1 | 7/2001 | Ziarno | 235/380 |
| 6,343,279 | B1 | 1/2002 | Bissonette et al. | 705/41 |
| 6,554,183 | B1 | 4/2003 | Sticha et al. | 235/379 |
| 6,738,749 | B1 | 5/2004 | Chasko | 705/17 |
| 2001/0027403 | A1 | 10/2001 | Peterson et al. | 705/4 |
| 2002/0002495 | A1 | 1/2002 | Ullman et al. | 705/21 |
| 2002/0019754 | A1 | 2/2002 | Peterson et al. | 705/4 |
| 2002/0087444 | A1 | 7/2002 | Dipiero et al. | 705/35 |
| 2002/0128879 | A1 | 9/2002 | Spears | 705/4 |
| 2002/0138376 | A1 | 9/2002 | Hinkle | 705/30 |
| 2002/0147678 | A1 | 10/2002 | Drunsic | 705/39 |
| 2003/0009355 | A1 | 1/2003 | Gupta | 705/2 |
| 2003/0061153 | A1 | 3/2003 | Birdsong et al. | 705/39 |
| 2003/0074234 | A1 | 4/2003 | Stasny | 705/4 |
| 2003/0130868 | A1 | 7/2003 | Coelho | 705/2 |
| 2003/0149594 | A1 | 8/2003 | Beazley et al. | 705/2 |
| 2003/0171953 | A1 | 9/2003 | Narayanan et al. | 705/2 |
| 2004/0064386 | A1 | 4/2004 | Goguen et al. | 705/34 |
| 2004/0249745 | A1 | 12/2004 | Baaren | 705/39 |
| 2005/0033677 | A1 | 2/2005 | Birdsong et al. | 705/35 |
| 2005/0080692 | A1 | 4/2005 | Padam et al. | 705/30 |
| 2005/0121511 | A1 | 6/2005 | Robbins et al. | 235/380 |

OTHER PUBLICATIONS

"Drugstore.com, Inc. and Evolution Benefits Make It Easier to Manage FSA-Eligible OTC Medication Expenses," *Business Wire*, p. 5224, Mar. 3, 2004.

O'Donnell, A., "IRS OKs Health Card Tech," *Insurance & Technology*, vol. 28, No. 13, p. 12, Dec. 2003.

"Payment Cards/Debit Cards . . . ," http://www.creativebenefits.com/paymentcards.htm, Nov. 25, 2003.

"SmartFlex Partners With U.S. Script to Launch State-of-Art Pharmacy Solution," *PR Newswire*, Oct. 3, 2003.

Carano, T., "IRS Guidance Provided on Debit Card Use," *EBMC Report*, Aug. 2003.

Evolution Benefits Update On the Treasury Guidance on Use of Debit Cards With Flexible Spending Accounts (FSAs) and Health Reimbursement Arrangements (HRAs), Jun. 23, 2003.

"Examples of Debit Card Programs in Wake of Guidance Included in IRS Ruling for FSAs and HRAs," *Spencer Benefits Reports*, Jun. 20, 2003.

Printout of Internet Documents From the Fringe Benefits Management Company at http://www.fbmc-benefits.com/, May 2001.

Printout of Internet Documents From the MedAdvantage Corporation at http://www.medadvantage.com/, May 2001.

Printout of Internet Documents From Med-i-Bank at http://www.medibank.com/, May 2001.

Anonymous, "IRS Branch Chief Fields Cafeteria Plan Queries," *Employee Benefit Plan Review*, vol. 53, No. 12, pp. 32-33, Jun. 1999.

Hamill, James R., "The Design and Operation of Cafeteria Plans," *Tax Adviser*, vol. 24, No. 10, pp. 657-664, Oct. 1993.

Kuriyan, J. G., "New PHO Concept Eliminates Middleman," *Computers in Healthcare*, vol. 13, No. 6, pp. 24(3), Jun. 1992.

"Condor Offers On-Line Verification Systems," *Chain Drug Review*, vol. 13, No. 18, p. RX5(1), Jun. 17, 1991.

"Eckerds' Prescription for Success is Electronic Claims," *Computers in Healthcare*, vol. 12, No. 6, p. 51, Jun. 1991.

Conn, J., "Instant Results: Blues Plans in Several States Begin Online Claims Adjudication," *Modern Physician*, vol. 5, Iss. 1, p. 6, Jan. 1, 2001.

"Payment Cards/Debit Cards . . . " [online], Retrieved from the Internet: http://www.crbenefits.com/paymentcards.htm.

METHOD AND SYSTEM FOR PROCESSING TRANSACTIONS INVOLVING ACCOUNTS FOR REIMBURSING MEDICAL EXPENSES OR PATIENT RESPONSIBLE BALANCES WITH MULTIPLE TRANSACTION SUBSTANTIATION MODES

PRIORITY

This application is a continuation of, claims priority to, and incorporates by reference in its entirety, the following: U.S. patent application Ser. No. 10/739,218, filed on Dec. 19, 2003, now U.S. Pat. No. 7,197,468 which is a continuation in part of U.S. patent application Ser. No. 09/878,891, filed Jun. 11, 2001 now U.S. Pat. No. 7,174,302.

BACKGROUND OF THE INVENTION

1. Field of the Invention

The present invention relates to systems and methods for processing transactions involving accounts for reimbursing medical expenses or patient responsible balances; more specifically, the present invention relates to a method and system for processing transactions involving those accounts that are handled by multiple entities having multiple transaction substantiation modes.

2. Background

In the United States, the Internal Revenue Service ("IRS") Code allows an employer to create accounts for reimbursing its employees with qualified medical expenses or patient responsible balances ("PRBs"). These accounts are hereinafter referred to as "reimbursing accounts". The IRS Code also determines the types of expenses which are reimbursable. For example, some reimbursable expenses are co-payments and deductibles for health care expenses, vision expenses, ambulance expenses, oxygen equipment, wheelchairs, prescription drugs, and the like.

One example of a reimbursing account is the flexible spending account (FSA). As understood in the art, a FSA is a pre-tax account used to reimburse qualified medical expenses or PRB which would otherwise be paid directly by the plan participant. A FSA can be funded by an employer, employees or both. It is sponsored by an employer and typically administered by a third-party administrator (TPA) and/or any other service agent(s) designated or contracted by the employer. Alternatively, an employer can sponsor and administer a FSA independently. Typically, the employee, i.e. account holder, designates a portion of his or her compensation into an FSA on a tax-free basis. The employee receives desired goods and services of which the employee's health insurance may pay for a portion or all of the cost. Generally, in the case of pharmacy transactions, the determination of the amount the employee's health insurance will pay is made by a pharmacy benefits manager (PBM) that is typically associated with the health insurance. Often, the employee is required to pay at least a percentage or flat fee, e.g., the PRB. If the out-of-pocket employee payment is a qualified expense under the IRS Code, the employee can be reimbursed from his/her FSA. FSAs provide benefits to employers and employees by saving both tax dollars. Further, employers increase employee morale and retention, enhance their status in recruiting and provide flexibility to their employees. Employees garner the advantages of budgeting for qualified expenses and directing how their FSA money is spent. As also understood in the art, other examples of a reimbursing account include the health reimbursable arrangement account (HRA), the medical savings account (MSA), and the like.

An employer, independently or through a TPA/service agent, can utilize one or more PBMs, in the case of pharmacy transactions, to administer reimbursing accounts to its employee population. For instance, an employer with an employee population situated in multiple localities may sponsor multiple local health plans in order to provide adequate health care coverage to all of its employees, wherein each health plan typically has its own PBM and PBM arrangement. Hence, the employer can have a particular PBM arrangement with each PBM through the associated health plan. Alternatively, the employer or its TPA/service agent can directly contract with multiple PBMs to administer the reimbursing accounts to the employee population.

As referred herein, the term "employee" or "employee population" includes the employee(s), the employee's spouse or partner, and/or the employee's dependent(s) that participate in the employer's program(s) involving accounts for reimbursing medical expenses or patient responsible balances.

SUMMARY OF THE INVENTION

U.S. patent application Ser. No. 09/878,891, filed Jun. 11, 2001 ("Parent Patent Application"), discloses a system and method for processing transactions involving accounts for reimbursing qualified medical expenses or PRBs, which assures that only allowed expenses are reimbursed through electronic substantiation, alleviates onerous paperwork, enables a customer (employee) to pay the PRB from such account without providing money at the point of sale (POS) through use of a payment card associated with the account, and/or maintains accurate records for review by the employee, employer and TPA/service agent.

There are a number of problems associated with electronic substantiation of transactions against reimbursing accounts of an employee population of a multi-PBM employer (i.e., an employer that utilizes multiple PBMs). As mentioned earlier, an employer, through its sponsored health plans, may have a particular arrangement with each of the multiple PBMs. Therefore, while the entire employee population may be issued payment cards for debiting reimbursable accounts, each employee may be treated differently at the POS based on the PBM associated with the employee (either through an employer-sponsored health plan or as designated by the employer). For instance, the employer, independently or through its TPA/service agent, may have an arrangement with some PBMs (real-time PBMs) to perform real-time substantiation of allowable pharmacy transactions and no arrangement at all for other PBMs. Consequently, if the employer provides a single/global real-time card transaction substantiation mode for its employee population, an employee associated with a real-time PBM can use his/her payment card to perform allowable pharmacy transactions at the POS in real-time transaction substantiation mode, an employee associated with a non-real-time PBM may be rejected at the POS if he/she attempts to use his/her payment card to perform allowable pharmacy transactions because the real-time transaction substantiation mode is not available. Furthermore, even with an associated real-time PBM, there is typically a waiting period from the time an employee activates a payment card to the time the data is available from the PBM to allow real-time transaction substantiation. Thus, the employee cannot use the payment card during such waiting period.

To avoid the above card transaction problem that may be experienced by those employees associated with a non-real-time PBM, the employer can forgo the advantages of real-time substantiation and subject its entire employee population to the more time consuming and costly retrospective substantiation mode, wherein card transactions by all employees are authorized and paid at the POS prior to substantiation, as discussed in more details later.

Thus, there exists a need for a system and method that can differentiate each employee and his/her associated card transaction substantiation mode and provide different card transaction substantiation modes to different employees in a particular employee population. Unfortunately, in many instances, the employer or its TPA/service agent, as the case may be, does not readily have PBM data at the employee or cardholder level to differentiate employees and their associated substantiation modes. This is problematic because there is no advance determination of those employees that are allowed to use their payment cards for real-time substantiation of allowable transactions and those that are not. Consequently, the employer may choose to avoid the confusion by denying its entire employee population real time substantiation of payment card transactions and instead require every payment card transaction that involves any of its employees to be subjected to the more time consuming and costly retrospective substantiation. Worse still, the employer may deny its entire employee population the convenient use of payment cards for reimbursing accounts altogether.

Thus, there also exists a need for a system and method for processing transactions involving accounts for reimbursing qualified medical expenses or PRBs which: allows advance determination of individual employees of a particular employer, their associated PBMs and associated transaction substantiation modes; assures that allowed payment-card expenses at the POS from only employees with associated real-time PBMs are substantiated in real time and reimbursed, and properly handles allowed expenses at the POS from other employees with retrospective substantiation of such expenses.

Accordingly, the preferred embodiments of the present invention provide a solution for a multi-PBM employer to allow all of its employees the ability to use their payment cards for debiting their reimbursing accounts for allowable transactions at the POS without requiring any additional work from the employer or its TPA/service agent, and wherein multiple transaction substantiation modes (such as real-time and retrospective modes) can be provided for the employee population of the particular multi-PBM employer.

The preferred embodiments of the present invention also provide a system and method for enabling a multi-PBM employer to distinguish its employees based on their associated PBMs and utilize both real-time and retrospective substantiation modes to process payment card transactions based on either the associated PBMs or the collection of PBM data at the employee level to determine use of a particular card transaction substantiation mode.

The preferred embodiments of the present invention further provide a "real-time where available" approach to substantiation of card transactions that enables an employer or its TPA/service agent to utilize both real-time and retrospective PBMs for a particular employee population, wherein the decision point of whether PBM data should be utilized in real-time can be at the current employer group level or brought down to the individual participant level.

Additional aspects and novel features of the invention will be set forth in part in the description that follows, and in part will become more apparent to those skilled in the art upon examination of the present disclosure.

BRIEF DESCRIPTION OF THE DRAWINGS

The preferred embodiments of the present invention are illustrated by way of example and not limited to the following figures.

DETAILED DESCRIPTION OF THE INVENTION

Reference is now made in detail to embodiments of the present invention, an illustrative example of which is illustrated in the accompanying attachments, showing a method and system for a "multi-PBM matching" solution that enables a particular multiple-PBM employer or its TPA to utilize a variety of electronic substantiation techniques for different PBMs.

Figure 1:
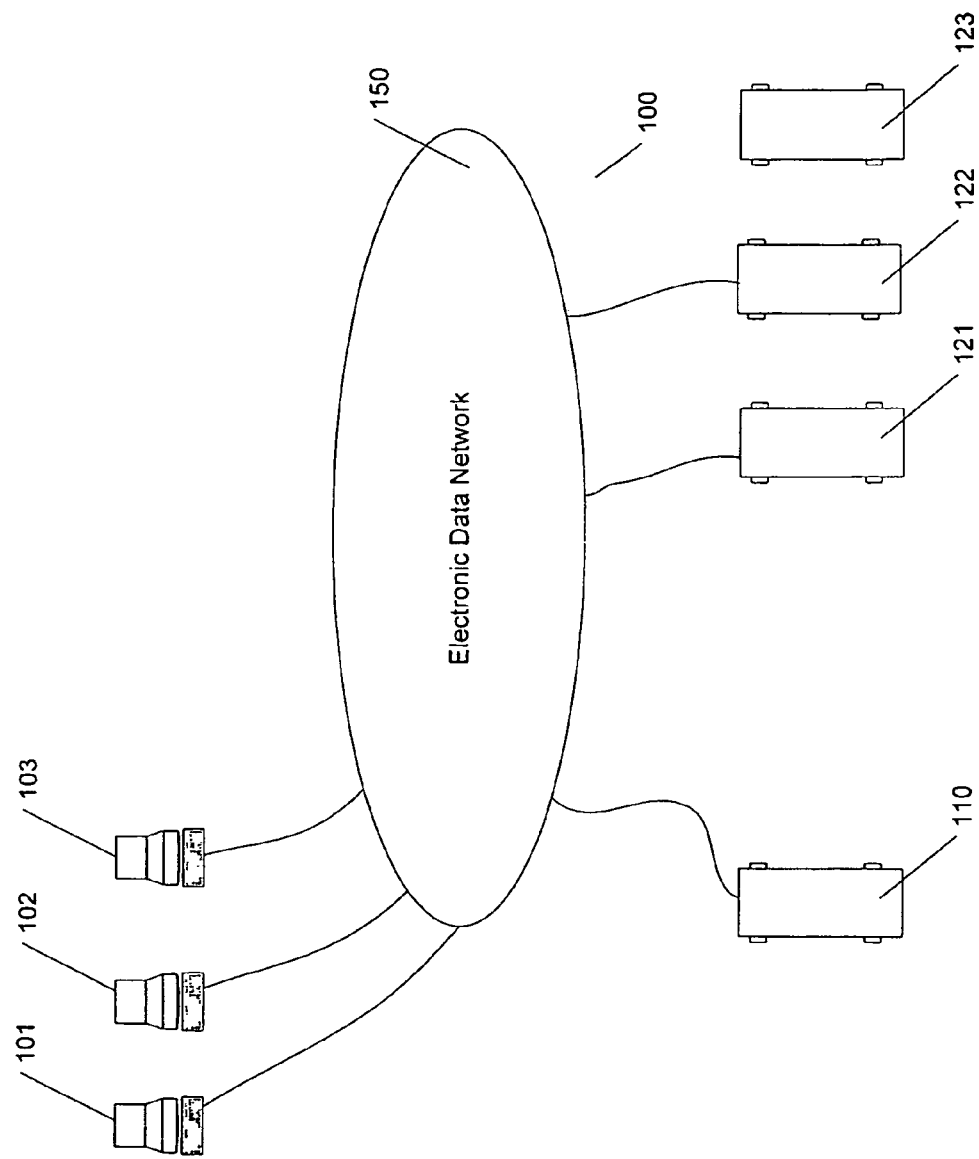
FIG. 1 depicts a system for a "multi-PBM matching" solution in accordance with an embodiment of the present invention.

Referring to FIG. 1, a schematic illustration of a system, designated generally by the reference numeral 100, provides access to an account for reimbursing qualified medical expenses or PRBs for participating employees 102a, 102b, and 102c of a sponsoring employer 104. As mentioned earlier, the reimbursing account can be an FSA, an HRA, an MSA, an HSA or the like. The system 100 includes a plurality of goods and/or service providers, such as pharmacies 110, a TPA 121, a multi-PBM service agent 120 for assisting the employer 104 or TPA 121 in servicing the multiple payors, and a plurality of payors, such as PBMs 130a-c. It should be noted that the service agent 120 only services those PBMs utilized by the employer with which the service agent 120 is a partner. Those PBMs are hereinafter referred to as "partner PBMs." Further, a partner PBM can be a real-time partner PBM or a non-real-time partner PBM. The employer 104, multi-PBM service agent 120, TPA 121, and the PBMs 130a-c can each have a server in communication with the distributed computing network 140 as noted in the Parent Patent Application and not reiterated herein.

Although only one employer and its three participating employees are illustrated, it is understood that a plurality of employers, each with one or more participating employees (hereinafter referred to as "participants"), may simultaneously reap the advantages and benefits of the subject disclosure. Similarly, only two pharmacies 110, one TPA 121, one multi-PBM service agent 120, and three PBMs 130a-130c are shown for simplicity; however, numerous pharmacies and/or other goods and service providers 110, TPAs 121, multi-PBM service agents 120, and PBMs and/or other payors 130 may simultaneously participate in the present disclosure.

The term "payor" is used herein to mean any entity that adjudicates claims for payment or reimbursement of qualified medical expenses under the IRS Code and is in a position to transmit data relating to such adjudicated transactions to a multi-PBM service agent 120 in accordance with the present invention. Claim adjudication typically involves determining whether the participant has insurance coverage, the amount to be paid by the respective insurer, and balance of the transaction amount owed by the participant. As indicated earlier, the balance of the transaction amount owed by the participant is referred to herein as the "patient responsible balance" or "PRB". The term "patient responsible balance" and acronym "PRB" as used herein do not require that the participant actually be a "patient" in the ordinary sense of the word; rather, this term and acronym simply refer to the balance of the transaction amount owed by the participant who frequently is, but need not be, a patient. The term "pharmacy benefits manager" and acronym "PBM" are used herein to refer to a specific type of "payor", and therefore contemplate, without limitation, any entity that adjudicates pharmacy transactions and provides data to the TPA 121 to substantiate whether the expenses involved in a pharmacy transaction are allowed for reimbursement under the IRS Code. In the preferred embodiment, the PBMs 130 adjudicate each pharmacy transaction, i.e., the PBMs determine whether a card holder has insurance coverage, the amount of the transaction to be paid by the respective insurer, and the PRB.

As referred herein, substantiation of payment-card transactions involving reimbursing accounts refers to the following process: 1) when a customer/participant uses his/her payment card linked to a reimbursing account to purchase goods or services from a goods or service provider, such as a pharmacy, the goods or service provider sends to a respective payor, such as a PBM, the claim information, including, for example, a customer or participant identifier, provider identifier, and purchase information; 2) the payor uses the claim information to adjudicate the claim, i.e., determines whether the participant has insurance coverage, the amount to be paid by the insurer, and the PRB; 3) the payor then sends back to the goods or service provider the PRB; 4) upon completing the transaction with the goods or service provider, the payor sends the transaction data (which preferably includes, among other information, the PRB) of the participant, directly or via one or more intermediaries, to a service agent of the employer (with whom the payor is a partner) for storage; 5) when the participant's payment card is processed through a POS device located at the goods or service provider, the participant-related information is sent to the service agent for a request to authorize payment of the PRB from the participant's reimbursing account; 6) the service agent then matches the payment authorization request with the transaction data received from the partner payor; and 7) the service agent authorizes the payment based on the payor data matching.

Likewise, as referred herein, real-time substantiation refers to the above substantiation process wherein the above steps 2 to 7 are performed (e.g., with electronic data transmission) while the customer is purchasing the goods or services at the POS so that payment authorization is based on the data matching and provided to the customer at the POS.

On the other hand, as referred herein, retrospective substantiation refers to the above substantiation process wherein payment authorization at above step 7 is provided to the customer/participant at the POS prior to the data matching in above step 6. Thus, the above steps 4 and 6 may not happen until after the transaction is completed at the POS, wherein transaction data of the participant subsequently can be transmitted from the payor, directly or via one or more intermediaries, to the service agent based on an existing arrangement between the service agent and the payor for payor data matching and retrospective substantiation. Alternatively, if there exists no arrangement for transferring transaction data from the payor to the service agent for retrospective matching, an audit letter can be sent out to the customer requesting the transaction receipt for substantiating the card swept at the POS, as understood in the art.

According to an embodiment of the present invention, the retrospective substantiation process can be described as follows. First, eligibility reports of eligible participants are periodically provided to the partner PBMs, as described later with regard to FIGS. 2A-B. Each of those partner PBMs with retrospective substantiation mode (hereinafter, "retrospective PBMs") uses the eligibility reports to extract all paid claims data, i.e., transaction data, from the service providers on a periodic basis, e.g., daily or weekly. The transaction data is then transmitted from the retrospective PBM to the service agent, which then loads such data into its system. The service agent then compares the transaction data with the payment authorization requests from the service providers which the service agent has previously authorized (i.e., settled card transactions). The comparison can be done using the following fields: member ID, date of the card transaction, and dollar amount.

In order to improve the accuracy of the substantiation process, only transaction data of those PBM transactions within a pre-defined period of time may be considered for matching purposes. For instance, the pre-defined period of time can be set to 30 days, i.e., all PBM transactions with a date of service in the 30 days prior to the settled card transaction are considered as eligible to be matched. The service agent uses matching logic to match the settled card transaction to all combinations of PRBs sent as part of the PBM transactions data. If the settled card transaction can be matched with one or more PBM transactions, the settled card transaction is set to a "matched" status. Additionally, any PBM transaction that has been used to make the match is also set to a "matched" status so that it will not be considered in future attempts to match other settled card transactions. If the settled card transaction cannot be matched, it is set to an "audit" status and additional documentation is required from the participant regarding the settled card transaction.

As may be recognized by those skilled in the pertinent art based on the teachings herein, although the goods and/or service providers in the illustrated embodiment are pharmacies 110, the system and method of the present invention contemplate any of numerous different types of goods and/or service providers in lieu of, or in addition to the pharmacies. For example, the goods and/or service providers 110 may include, without limitation, physicians, hospitals, ambulatory surgery centers, vision care specialists, dentists, and the like. One exemplary method of obtaining the necessary data from transactions, pharmacy or otherwise, is to receive the necessary data from the relevant health insurer or TPA. As mentioned earlier, another alternative method would be for the multi-PBM service agent 120 to receive the necessary transaction data to populate its databases from one or more clearing houses, or one or more other intermediaries (e.g., switches or some other entities), which the transactions are routed through. Further still, although the payors in the illustrated embodiments are PBMs 130a-c, the system and method of the present invention contemplate in lieu of, or in addition to the PBMs, any of numerous different types of entities that are currently, or later become known for performing the function of adjudicating claims for payment or reimbursement of qualified medical expenses under the IRS Code or any other present or future governmental law, rules and/or regulations. Likewise, the phrase "multi-PBM" can be rephrased "multi-payor" should the payor be an entity other than a PBM, and a payment-card transaction for substantiation can be an allowable transaction other than a pharmacy transaction.

As mentioned earlier, each employee/participant has an associated PBM (either through an employer-sponsored health plan or as designated by the employer) for administering his/her reimbursing account. Consequently, each PBM may be provided in advance a list of the associated employee(s) and their relevant information for administering their reimbursing accounts. Each PBM can store such information in its own PBM eligibility database.

Each of the entities within the system 100 communicates over the distributed computing network 140 with commonly known communication links. Each of the entities within the system 100 include internal architectures, interfaces, and communication devices (such as modems, T1 lines, etc.) to enable processing, communication and security. For the purpose of simplicity and clarity, a detailed description of the same is omitted because they are well known in the art. The entities can communicate via direct network connection (e.g., a private data network), satellite, and the like. In another embodiment, the distributed computing network 140 is at least partly a public data network such as the Internet.

According to an embodiment of the present invention, within a given employee population 102a-102c of an employer 104, the multi-service agent 120 is provided with a capability to determine the appropriate action to take for a particular employee without requiring the service agent 120 to collect and maintain PBM data at the employee level. Thus, the service agent 120 is not required to keep track of each employee and his/her associated PBM, and whether the associated PBM is a real-time partner PBM. For example, if the service agent 120 receives transaction data of a participant, e.g., employee 102a, from a real-time partner PBM, e.g., PBM 130a, the employee 102a then will be set for real-time transaction substantiation when certain conditions are met. If the service agent 120 does not receive transaction data of a participant, e.g., employee 102b, because he/she is associated with a non-real-time partner PBM, e.g., PBM 130b, that employee 102b will be set for retrospective transaction substantiation. The process for this substantiation approach is described next.

Prior to the employees 102a-c taking advantage of the disclosed system to perform payment-card transactions, an employer 104 contracts with a TPA 121. In turn, the TPA 121 contracts with a multi-PBM service agent 120 in order to offer the system and method of the invention as a benefit to those employees 102a-c that participate. If the employer 104 is administering the reimbursing account program independently, the employer 104 can contract directly with the multi-PBM service agent 120.

Figure 2A:
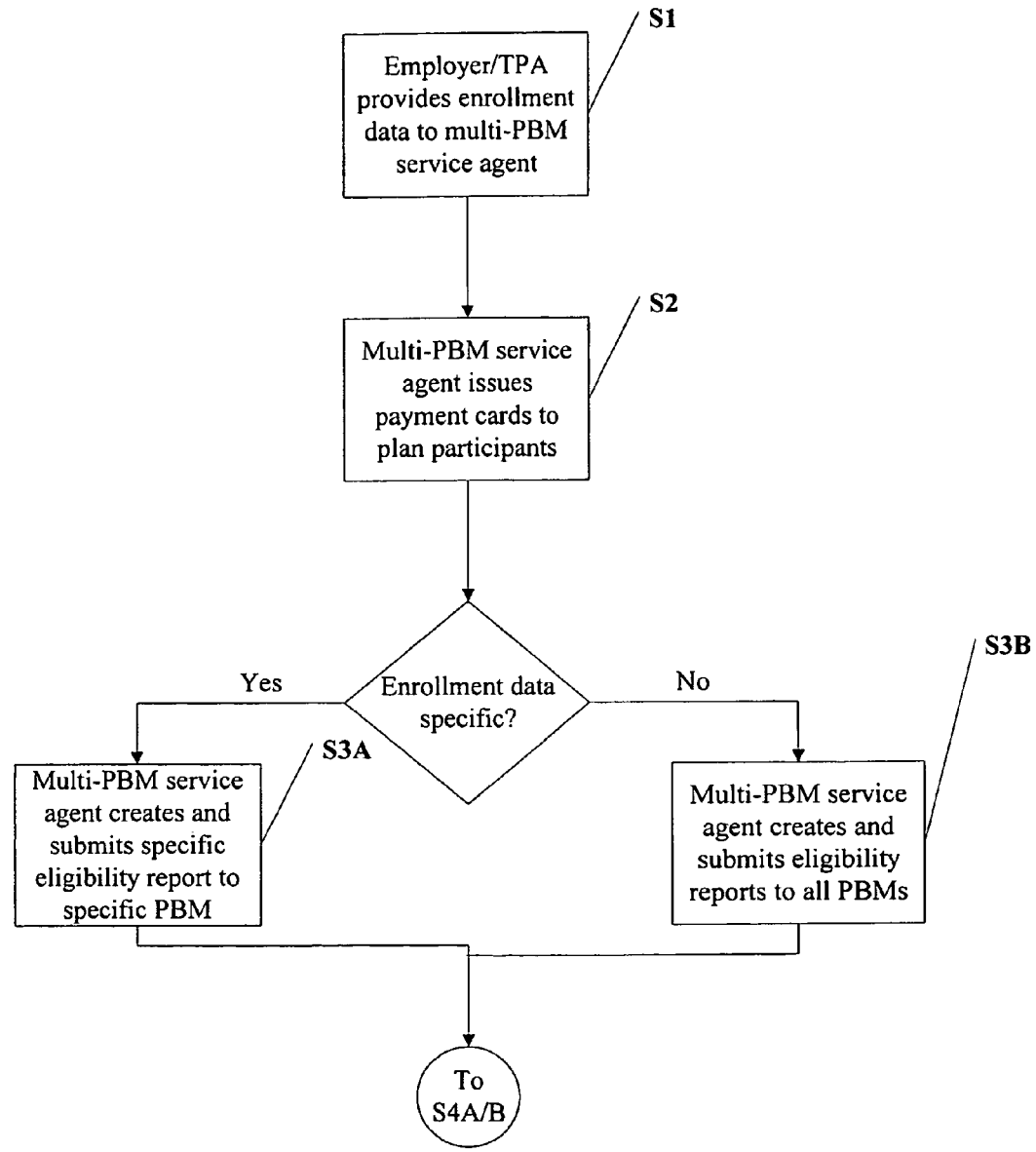
FIGS. 2A-B depict a process flow for the initial employer set up by a multi-PBM service agent, in accordance with various embodiments of the present invention.
Figure 2B:
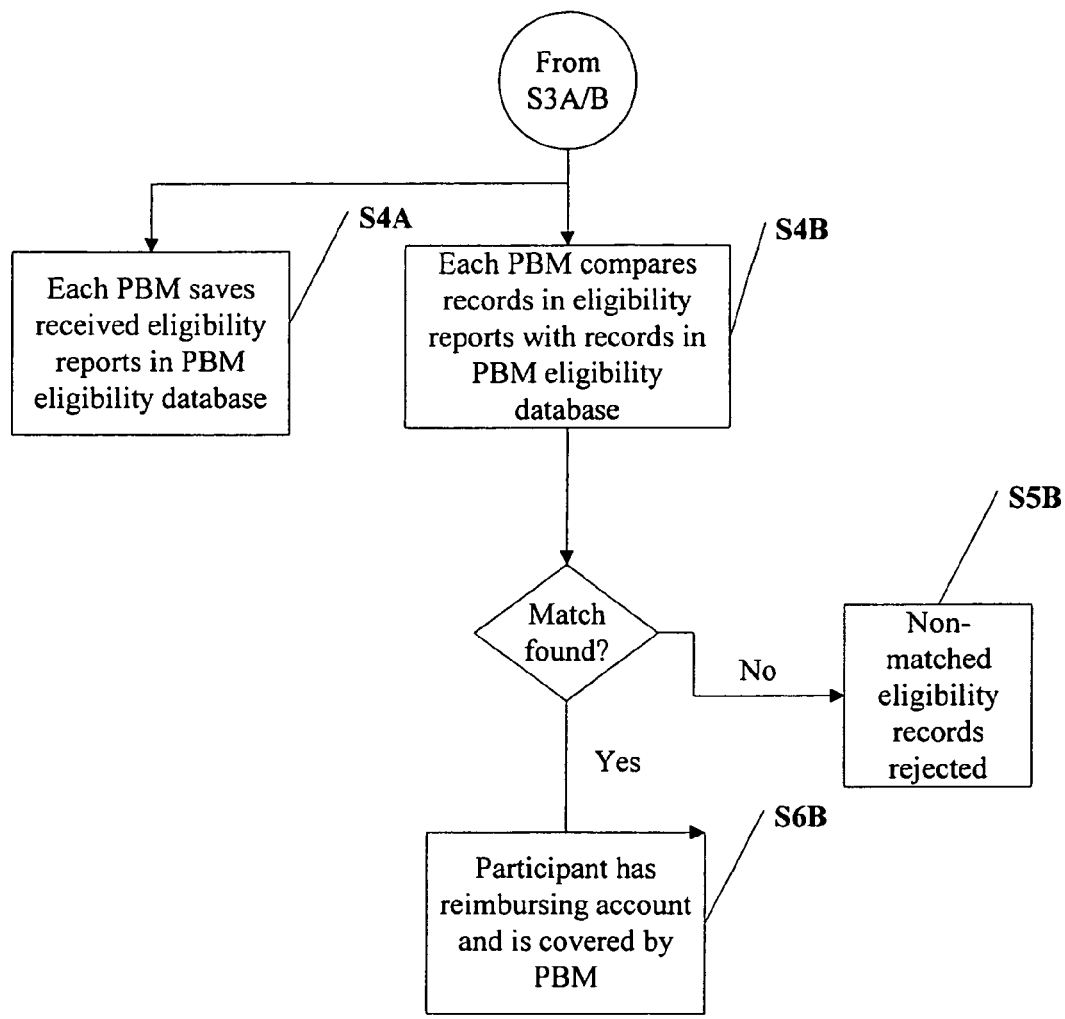

Referring to FIGS. 2A-B, multiple embodiments of the present invention are now described. Upon engagement with the multi-PBM service agent 120, the employer 104 or TPA 121, as the case may be, provides enrollment data relating to the eligibility of the participants 102a-c to the multi-PBM service agent 120 to populate its eligibility database at S1. The enrollment or eligibility data can include a participant identifier and a record type. In one embodiment, the participant identifier is the participant's social security number. In another embodiment, the participant identifier is a plan participant number assigned by the employer 104, the TPA 121, or the associated PBM. The record type indicates whether to add or terminate the employee 102 associated with the social security number. In one embodiment of the present invention, the enrollment/eligibility data includes specific PBM data for each employee to indicate his/her associated PBM and/or associated card transaction substantiation mode. The specific PBM data can be provided by the employer or an other entity, such as a PBM or health plan, that has such information and is set up to provide such information to the service agent 120. Thus, the decision point of which substantiation mode should be used is available at the employer level. In another embodiment of the present invention, the enrollment/eligibility data does not include such specific PBM data.

Depending upon the urgency, the enrollment/eligibility data may be transferred to the service agent 120 immediately, hourly, daily, monthly or the like. For instance, if the eligibility data is received daily, the service agent 120 will populate its eligibility database on a nightly basis.

At S2, based on the received eligibility data, which the service agent 120 uses to populate its eligibility database, the service agent 120 issues payment cards to the participating employees 102a-c for debiting their reimbursing accounts. The employees 102a-c can then activate their payment cards upon receipt. Alternatively, the payment cards can be activated prior to issuance to the employees 102a-c. In the first embodiment wherein the enrollment/eligibility data includes specific PBM data, at S3A, the service agent 120 will create a specific eligibility report for each of the plurality of partner PBMs 130a-c utilized by the employer 104, listing those employees that are current plan participants and associated with the particular PBM (based on the specific PBM data) and periodically submit the particular report to the particular partner PBM. In the second embodiment wherein the enrollment/eligibility data does not include specific PBM data, at S3B, the service agent 120 will create eligibility reports listing those employees that are current plan participants and periodically submit all such reports to each of the plurality of partner PBMs 130a-c that are utilized by the employer 104. For this embodiment, it should be noted that all eligibility reports are forwarded to each and every one of the partner PBMs 130a-c associated with that employer because the service agent 120 does not possess the employee-level information of associated partner PBMs nor does it receive such information from the employer 104 or TPA 121, which also does not collect such detailed information as mentioned earlier.

At S4A, each partner PBM can load up the specific or all eligibility report(s) received from the service agent 120 into its PBM eligibility database. Each partner PBM requires the eligibility report(s) in order to prevent transmitting to the multi-PBM agent 120 transaction data in connection with ineligible employees to whom it is not associated and in order to ensure transmission of data of eligible employees with whom it is associated. Alternatively, at S4B, each partner PBM can pare down the received eligibility report(s) by comparing such report(s) with information previously saved in its PBM eligibility database, as noted earlier, for a match based upon a participant identifier, such as the social security number or participant number. At S5B, if a matching record is not found, i.e., one of the participants 102a-c is not currently in the PBM eligibility database maintained by a particular partner PBM, the eligibility record for such participant in the eligibility reports is rejected. However, if a matching record is found, the PBM eligibility database will indicate that the particular participant has a reimbursing account and is associated with the particular partner PBM at S6B.

During the aforementioned initial employer setup by the service agent 120, all participants in the particular plan will be setup with a "PBM Activation Pending" status by the service agent 120 and for retrospective co-payment matching as a default. This status will apply for a predetermined initial time period (e.g., 14 days) following the issuance of payment cards to plan participants. The duration of the predetermined time period can be set as desired by the service agent 120 based on any number of criteria as also desired by the service agent 120.

In the second embodiment wherein the enrollment/eligibility data does not include specific PBM data, subsequent to the initial predetermined time period following the activation (e.g., on the 15$^{th}$ day after activation), the service agent 120 will review each account to determine if PBM transaction data, i.e., transaction data sent by a partner PBM, was received for that participant. If a transaction for a participant was not received, the particular participant will be set to retrospective matching and designated as such; for instance, the participant can be given a second status of "PBM Retro" (or any other name as desired). However, if a transaction for a participant has been received from a real-time partner PBM, the particular participant will be set for real-time matching of subsequent transactions at the POS and designated as such; for instance, the participant can be given a third status of "PBM Real Time" (or any other name as desired). Hence, a participant can have one of the following PBM statuses: 1) PBM Activation Pending, wherein the participant is in the initial time period and set to retrospective transaction substantiation mode (i.e., no real-time PBM matching is required); 2) PBM Retro, wherein the participant is beyond the initial time period but still set to retrospective transaction substantiation mode; and 3) PBM Real Time, wherein the participant is beyond the initial time period and set to real-time transaction substantiation mode (i.e., real-time PBM matching is required).

However, if the particular participant has been set to retrospective matching beyond the initial time period, i.e., it has a status of PBM Retro, and the agent 120 receives a PBM transaction for the same participant from a real-time partner PBM, the PBM Real Time status change logic applies, wherein the participant's status can automatically be changed to real-time matching, i.e., PBM Real Time. This change can happen instantly upon receipt of the transaction from the real-time partner PBM. No additional eligibility data is required to utilize this function because the agent 120 is provided with the ability to automatically and dynamically determine the appropriate status for a particular plan participant "behind the scenes" based upon receipt of PBM transactions.

In the first embodiment wherein the enrollment/eligibility data includes specific PBM data, subsequent to the predetermined initial time period following the activation (e.g., on the 15$^{th}$ day after activation), a participant can be given a status of "PBM Real Time" regardless whether a PBM transaction has been received for such participant from a real-time partner PBM. This is because the specific PBM data for the participant would have indicated his/her association with a real-time partner PBM. Hence, such participant can have one of the following PBM statuses: 1) PBM Activation Pending, wherein the participant is in the initial time period and set to retrospective transaction substantiation mode (i.e., no real-time PBM matching is required); or 2) PBM Real Time, wherein the participant is beyond the initial time period and set to real-time transaction substantiation mode (i.e., real-time PBM matching is required). Of course, if the specific PBM data for the participant indicates his/her association with a non-real-time partner PBM or retroactive substantiation mode, the participant will be set to retrospective transaction substantiation mode (i.e., "PBM Retro" status).

Figure 3A:
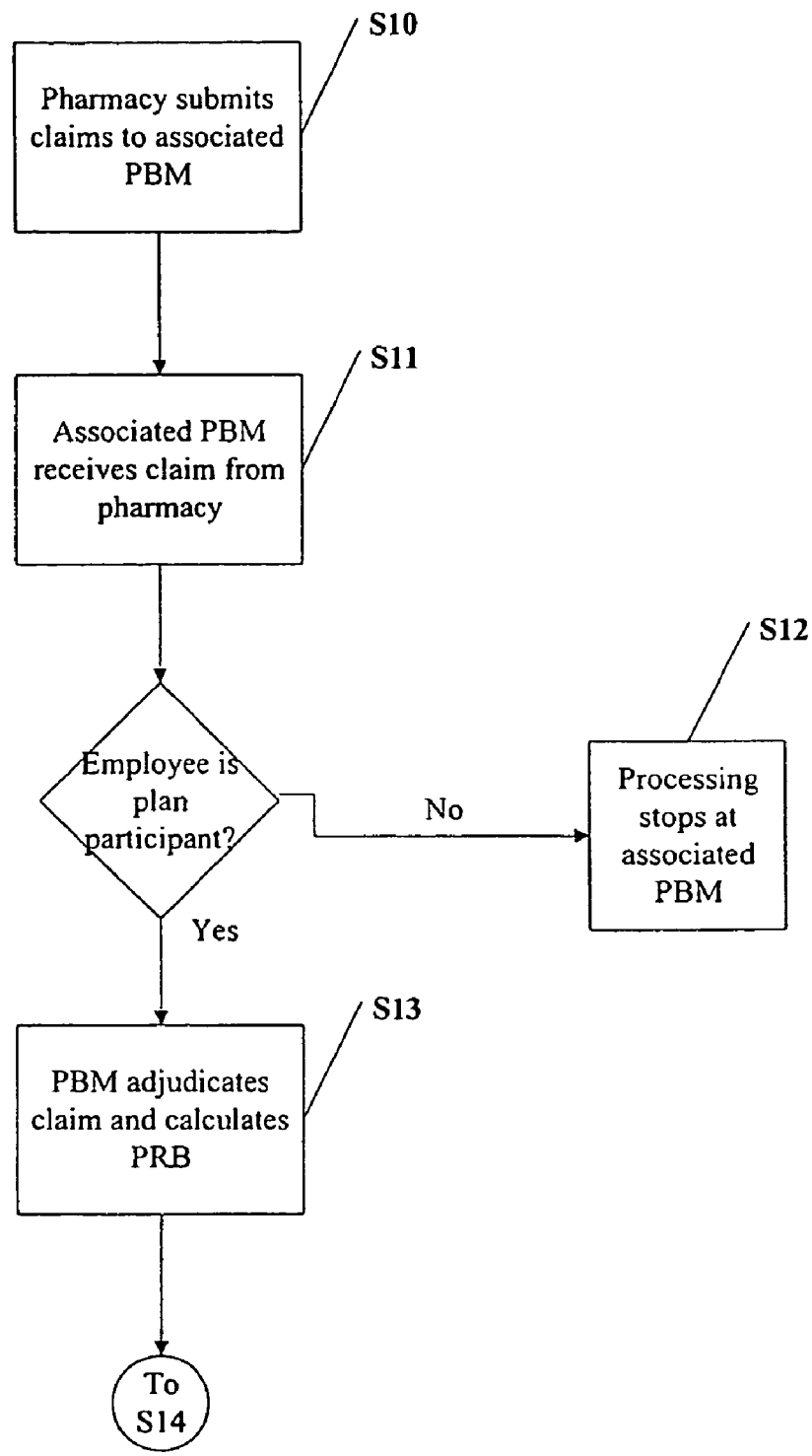
FIGS. 3A-B depict a process flow for the "multi-PBM matching" solution in accordance with an embodiment of the present invention.
Figure 3B:
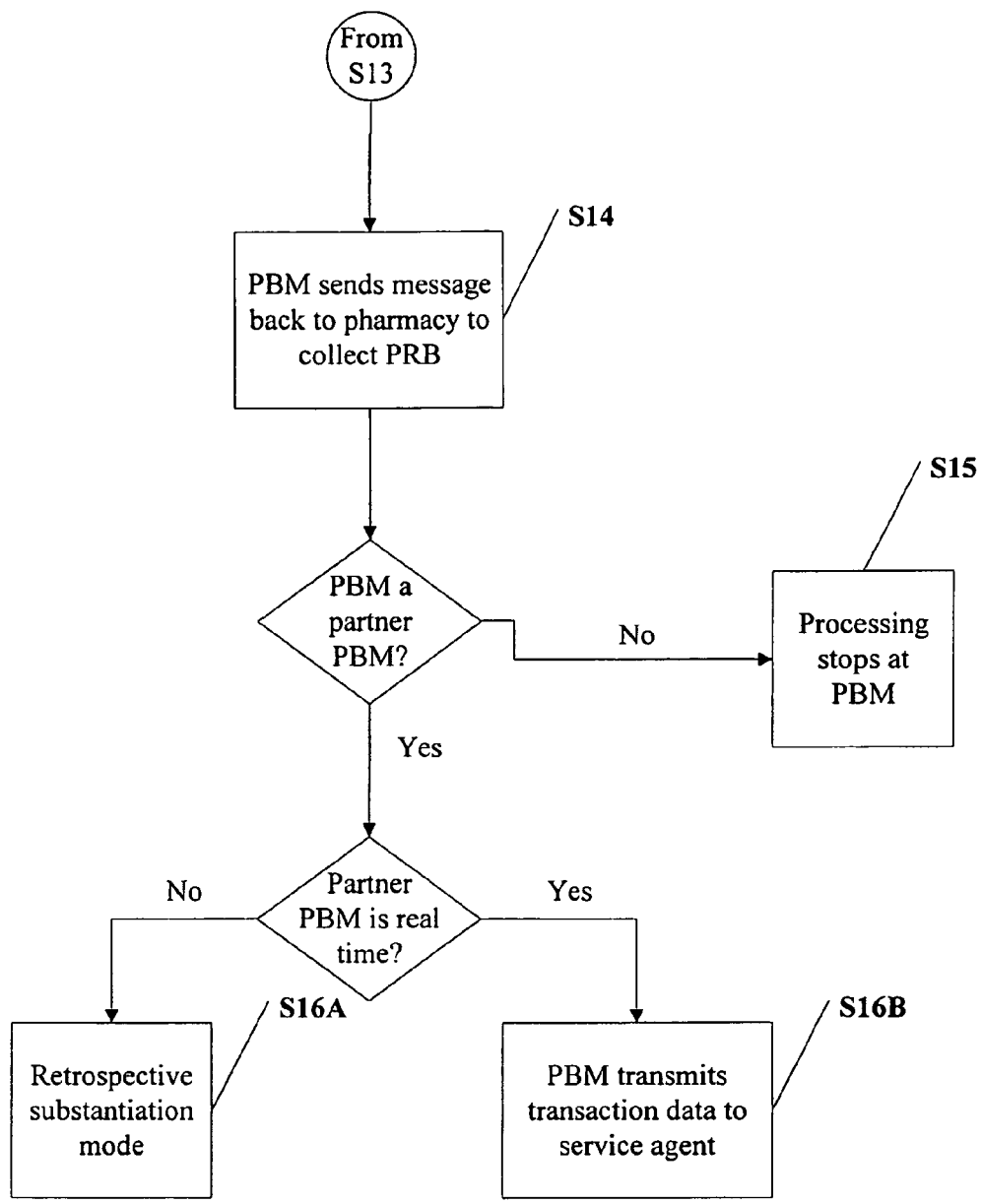

Referring to FIGS. 3A-B, scenarios are now provided to demonstrate the system and method of the present invention subsequent to the aforementioned initial employer set up. In all scenarios, an employee 102a begins a purchase, e.g., filling a prescription, at a goods and/or service provider, e.g., a pharmacy 110. As is customary the employee 102a provides insurance information to the pharmacy 110. At S10, the pharmacy 110 submits a claim to an associated one of the PBMs 130a-c used by the employer 104, e.g., PBM 130a, based on the provided insurance information, as understood in the art. The electronic data interchange to a PBM preferably occurs over a network in a secure environment as is known to those skilled in the art and, therefore, is not further described herein.

At S11, the PBM 130a receives the claim from the pharmacy 110, wherein it compares the claim data with the stored eligibility reports that it previously received from the service agent 120 to determine whether the employee is an eligible plan participant. At S12, if the employee 102a is not an eligible plan participant, processing is halted at the PBM 130a and the employee's claim is rejected. However, at S13, if the employee 102a is an eligible plan participant, the PBM 130a adjudicates the claim, i.e., calculates the payments to be made by the employee's insurance plan and the PRB. At S14, the PBM 130a then transmits a message to the pharmacy 110 indicating the PRB. At S15, if the particular PBM is not a partner PBM, processing at the PBM stops and the PBM will not send the transaction data of the participant 102a to the multi-PBM service agent 120 at all. At S16A, if the PBM 130a is a non-real-time partner PBM, retrospective transaction substantiation mode, as described earlier, would then be used for any card transaction associated with the pharmacy claim (i.e., PBM transactions data is used for subsequent matching with the card transaction). However, at S16B, if the PBM 130a is a real-time partner PBM, provided the PRB is greater than zero, processing at the PBM 130a continues wherein the PBM 130a transmits transaction data to the multi-PBM service agent 120 for real-time substantiation of the pharmacy claim. As mentioned earlier, the multi-PBM service agent 120 can receive the transaction data from the payor (e.g., PBM) directly or via one or more intermediaries, including the employer, the TPA or any other entities. It should be noted that S10-S15 apply regardless of whether the specific PBM data was received by the service agent 120.

The transaction data can include the participant identifier, such as an employee social security number, the time and date of the transaction and the PRB. If the PRB is less than or equal to zero, the PBM takes no action and the processing terminates. When the multi-PBM service agent 120 receives the transaction data from a real-time partner PBM, it retrieves the card holder identifier associated with the payment card of the employee 102a and the PRB based on the participant identifier in the transaction data, as described in the Parent Patent Application.

Figure 4:
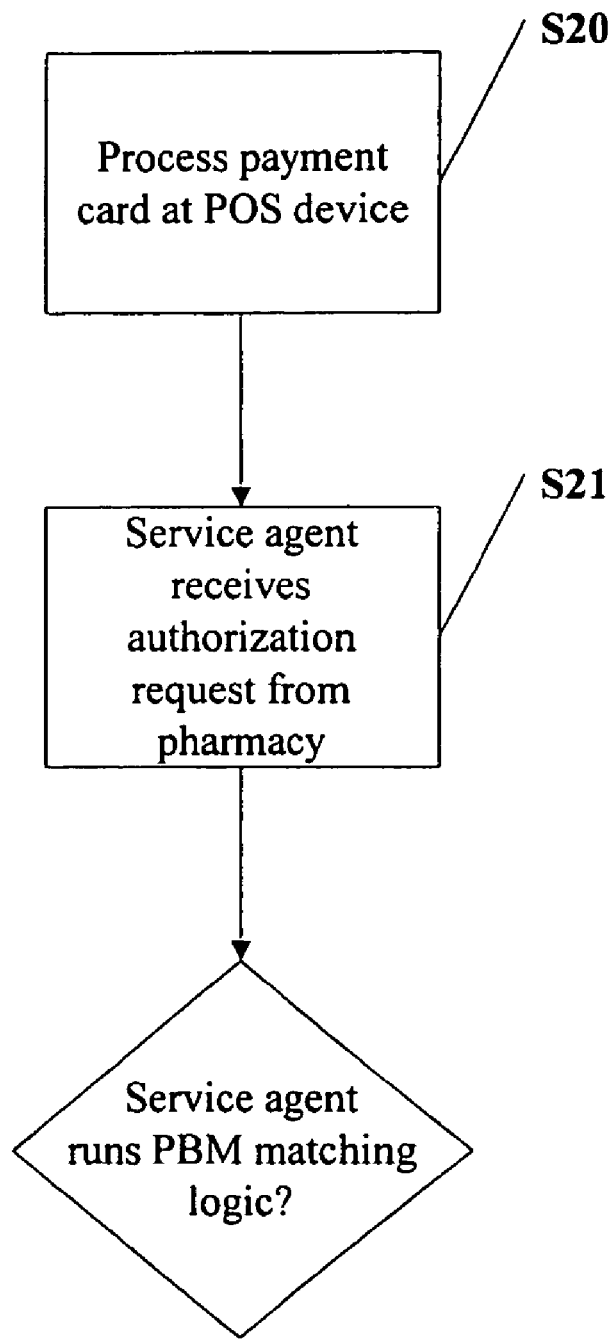
FIG. 4 depicts a process flow for real-time PBM matching in accordance with an embodiment of the present invention.

Referring to FIG. 4, when the employee 102a receives his/her prescription, the pharmacy 110 requests payment of the PRB. In order to enable payment of the PRB directly from the reimbursing account at that time and alleviate the need, subsequently, to file a reimbursement request to the TPA 121, the participant 102a provides his/her payment card to the pharmacy 110. At S20, the pharmacy 110 or participant 102a preferably applies the payment card at a POS device, such as a magnetic card reader, for processing similar to the method employed with a traditional credit or payment card. However, as may be recognized by those of ordinary skill in the pertinent art based on the teachings herein, the payment card information may be processed and transmitted by the pharmacy or other goods or service provider in any of numerous other ways that are currently, or later become known for performing this function. For example, the reimbursing account information on the payment card may be input by keyboard or other input device or accessed by a card reader device depending on the type of card used (e.g., chip reading, magnetic or magnetic emulation reading, radio frequency reading, smart card or chip reading) for collection and transmission to the service provider as disclosed herein. At S21, the multi-PBM service agent 120 receives the authorization request as a result of reading the payment card or otherwise inputting the reimbursing account information. The service agent 120 then runs the PBM matching logic (as described in the Parent Patent Application) or not, as the case may be, in accordance with the scenarios described below.

In a first scenario, the participant's PBM status is initially set to "PBM Activation Pending," and the service agent 120 receives no PBM transaction from any of the partner PBMs 130a-c prior to the authorization request from the pharmacy. When the participant swipes the payment card in the pharmacy for authorization, and all other authorization validations are successful, the service agent 120 will authorize the transaction. In this first scenario, no real-time PBM matching is required, and the service agent 120 will perform retrospective substantiation of the claim later.

In a second scenario, the participant's PBM status is initially set to "PBM Retro", and the service agent 120 has not received any PBM transaction from any of the partner PBMs 130a-c prior to the authorization request from the pharmacy. When the participant applies the payment card at the pharmacy for authorization, and all other authorization validations are successful, the service agent 120 will authorize the transaction. In this second scenario, no real-time PBM matching is required because of the participant's PBM status, and the service agent 120 will perform retrospective substantiation of the claim later.

In a third scenario, the participant's PBM status is initially set to "PBM Activation Pending", and the service agent 120 receives a PBM transaction from one of the partner PBMs 130a-c prior to the authorization request from the pharmacy. This indicates that the participant has an associated PBM that is a real-time partner PBM, but the aforementioned initial predetermined time period has not expired. Therefore, the participant's status remains "PBM Activation Pending" notwithstanding the receipt of the PBM transaction until the expiration of the initial predetermined time period. When the participant swipes the payment card in the pharmacy for authorization, and all other authorization validations are successful, the service agent 120 will authorize the transaction. In this third scenario, even though the service agent 120 receives a PBM transaction, PBM matching is still not required because the participant's status remains "PBM Activation Pending".

In a fourth scenario, the participant's PBM status is initially set to "PBM Retro", and the service agent 120 receives a PBM transaction from one of the partner PBMs 130a-c prior to the authorization request from the pharmacy. This indicates that the participant has an associated PBM that is a real-time partner PBM. Upon receipt of the PBM transaction from a PBM, the aforementioned PBM Real Time status change logic applies and the participant's PBM status immediately changes to "PBM real-time." When the participant applies the payment card at the pharmacy for authorization, and all other authorization validations are successful, the service agent 120 will authorize the transaction once it performs a PBM matching and there is a successful match. Thus, real-time PBM matching is required in this scenario.

In a fifth scenario, the participant's PBM status is initially set to "PBM Real Time", and the service agent 120 receives a PBM transaction from one of the PBMs 130a-c prior to the authorization request from the pharmacy. This indicates that the participant has an associated PBM that is a real-time partner with the service agent 120. When the participant swipes the payment card in the pharmacy for authorization, and all other authorization validations are successful, the service agent 120 will authorize the transaction once it performs a PBM matching and there is a successful match. In this fifth scenario, because the service agent 120 receives a PBM transaction and the participant's status is set to "PBM Real Time", as noted earlier, real-time PBM matching is required.

Accordingly, the "multi-PBM matching" solution of the present invention allows the employer 104 or TPA 121 to use a variety of techniques to substantiate pharmacy card transactions, rather than a lowest common denominator approach. The TPA is able to achieve the benefits of real-time PBM matching for those participants covered by one of the real-time PBM partners, but allows members covered by another substantiation method (i.e. retrospective PBM matching or retrospective co-payment matching) to use their card in the pharmacy. The solution also alleviates the typical waiting period for use of the card in the pharmacy after card activation. It further alleviates denials as a result of members attempting to purchase scripts filled prior to card activation.

Although the invention has been described with reference to these preferred embodiments, other embodiments could be made by those in the art to achieve the same or similar results. Variations and modifications of the present invention will be apparent to one skilled in the art based on this disclosure, and the present invention encompasses all such modifications and equivalents.

The invention claimed is:

1. A computer implemented method for processing a transaction involving an account for reimbursing qualified medical expenses and/or patient responsible balances (PRBs), comprising the steps of:
   receiving enrollment data of participants electing to perform payment-card transactions using accounts for reimbursing qualified medical expenses and/or PRBs;
   assigning a status to the participant from one of a first and second statuses;
   receiving from a goods or service provider a request to authorize payment of a qualified medical expense and/or PRB against an account associated with a participant in connection with a first sales transaction between the participant and the goods or service provider;
   in response to the participant's assigned status being of the first status, electronically performing a real-time substantiation of the first sales transaction using a computerized system, authorizing payment of the qualified medical expense and/or PRB against the associated account, and communicating to the goods or service provider authorization of payment of the qualified medical expense and/or PRB against the associated account, wherein the communicating the authorization occurs subsequently to the real-time substantiation; and
   in response to the participant's assigned status being of the second status, communicating to the goods or service provider authorization of payment of the qualified medical expense and/or PRB against the associated account, effecting the payment of the qualified medical expense and/or PRB against the associated account, and electronically performing a retrospective substantiation of the first sales transaction using a computerized system, wherein the retrospective substantiation is performed subsequently to the communication of the authorization.

2. The computer implemented method of claim 1 wherein assigning the status to the participant comprises assigning the first status to the participant upon an expiration of a predetermined initial time period and a receipt of transaction data associated with the participant's one or more sales transactions.

3. The computer implemented method of claim 1 wherein assigning the status to the participant comprises assigning the second status to the participant upon a receipt of an assignment of the retrospective substantiation to be performed with the participant.

4. The computer implemented method of claim 1 wherein assigning the status to the participant comprises assigning the second status to the participant when the participant is within a predetermined initial time period.

5. The computer implemented method of claim 1 wherein performing the real-time substantiation comprises:
  receiving transaction data associated with the participant's one or more sales transactions;
  comparing the transaction data with the first sales transaction to find a match of one or more pieces of the transaction data with the first sales transaction; and
  in response to the matching, removing the matched one or more transaction data pieces from the transaction data for future comparisons.

6. The computer implemented method of claim 1 wherein communicating to the goods or service provider comprises communicating to the goods or service provider authorization of payment of the qualified medical expense or PRB against the associated account prior to performing the retrospective substantiation.

7. The computer implemented method of claim 6 wherein performing the retrospective substantiation comprises:
  receiving transaction data associated with the participant's one or more sales transactions;
  comparing the transaction data with the first sales transaction to find a match of one or more pieces of the transaction data with the first sales transaction; and
  in response to the matching, removing the matched one or more transaction data pieces from the transaction data for future comparisons.

8. The computer implemented method of claim 7 wherein the participant's one or more sales transactions have been serviced in a predetermined period of time prior to a date of receiving from the goods or service provider the request to authorize payment of the qualified medical expense and/or PRB.

9. The computer implemented method of claim 1 wherein performing the retrospective substantiation comprises:
  receiving transaction data associated with the participant's one or more sales transactions;
  comparing the transaction data with the first sales transaction to find a match of one or more pieces of the transaction data with the first sales transaction; and
  in response to no matching of any of the transaction data pieces with the first sales transaction, requesting additional information from the participant regarding the first sales transaction.

10. The computer implemented method of claim 1 further comprising issuing to the participants payment-cards linked to the accounts based on the enrollment data and receiving notices of activation of the issued payment-cards from the participants.

11. A computer implemented method for processing transactions involving accounts for reimbursing qualified medical expenses and/or patient responsible balances (PRBs), comprising:
  receiving enrollment data of participants electing to perform payment-card transactions using accounts for reimbursing qualified medical expenses and/or PRBs;
  assigning a first status to a first participant;
  assigning a second status to a second participant, wherein the first status and second status cause different types of substantiation;
  receiving from a first goods or service provider a request to authorize payment of a qualified medical expense and/or PRB against an account associated with a first participant in connection with a first sales transaction between the first participant and the first goods or service provider;
  receiving from a second goods or service provider a request to authorize payment of a qualified medical expense and/or PRB against an account associated with a second participant in connection with a second sales transaction between the second participant and the second goods or service provider;
  in response to the participant's assigned status being of the first status, electronically performing a real-time substantiation of the first sales transaction using a computerized system, providing authorization of payment of the qualified medical expense and/or PRB against the associated account, and communicating to the goods or service provider authorization of payment of the qualified medical expense and/or PRB against the associated account, wherein the communicating the authorization occurs subsequently to the real-time substantiation; and
  in response to the second participant's assigned second status, electronically performing a second substantiation of the second sales transaction using a computerized system, the second substantiation being a retrospective substantiation of the second sales transaction, and communicating to the second goods or service provider authorization of payment of the qualified medical expense and/or PRB against the account associated with the second participant, wherein the retrospective substantiation is performed subsequently to the communication of the authorization.

12. The computer implemented method of claim 11 wherein performing the first substantiation comprises:
  receiving transaction data associated with the first participant's one or more sales transactions;
  comparing the transaction data with the first sales transaction to find a match of one or more pieces of the transaction data with the first sales transaction; and
  in response to the matching, removing the matched one or more transaction data pieces from the transaction data for future comparisons.

13. The computer implemented method of claim 11 wherein performing the second substantiation comprises:
  receiving transaction data associated with the second participant's one or more sales transactions;
  comparing the transaction data with the second sales transaction to find a match of one or more pieces of the transaction data with the second sales transaction; and
  in response to the matching, removing the matched one or more transaction data pieces from the transaction data for future comparisons.

14. The computer implemented method of claim 11 wherein the second participant's one or more sales transactions have been serviced a predetermined period of time prior to a date of receiving from the second goods or service provider the second request to authorize payment of the qualified medical expense and/or PRB.

15. The computer implemented method of claim 11 further comprising issuing to the participants payment-cards linked to the accounts based on enrollment data and receiving notices of activation of the issued payment-cards from the participants.

16. The computer implemented method of claim 15 further comprising creating eligibility reports of the participants based on the received notices of activation and providing the eligibility reports to all the payors in the list.

17. The computer implemented method of claim 11 wherein the request to authorize payment is based on one of the participants using one of the issued payment-cards at the goods or service provider.

18. The computer implemented method of claim 11 wherein the first goods or service provider and the second goods or service provider are the same.

19. The computer implemented method of claim 11 wherein the first goods or service provider and the second goods or service provider are different.

20. The computer implemented method of claim 11 wherein the participants are members of a single organization.

* * * * *